United States Patent [19]

Eppstein et al.

[11] Patent Number: 4,680,267
[45] Date of Patent: Jul. 14, 1987

[54] FERMENTOR CONTROL SYSTEM

[75] Inventors: Lee B. Eppstein, New Brunswick; Robert D. Mohler, Bridgewater; Shaul Reuveny, Highland Park, all of N.J.

[73] Assignee: New Brunswick Scientific Company, Inc., Edison, N.J.

[21] Appl. No.: 707,363

[22] Filed: Mar. 1, 1985

[51] Int. Cl.$^4$ ............................................. C12M 1/36
[52] U.S. Cl. .................................. 435/289; 435/291; 435/315; 435/807
[58] Field of Search .................. 435/289, 290, 291, 3, 435/313, 315, 807

[56] References Cited

U.S. PATENT DOCUMENTS

| | | | |
|---|---|---|---|
| 3,926,738 | 12/1975 | Nyiri et al. | 435/290 |
| 3,941,662 | 3/1976 | Munder et al. | 435/289 |
| 4,154,652 | 5/1979 | Sawamura et al. | 435/3 |
| 4,424,559 | 1/1984 | Lorincz et al. | 435/3 |

Primary Examiner—Larry Jones
Assistant Examiner—Noah Kamen
Attorney, Agent, or Firm—Blum Kaplan

[57] ABSTRACT

A method and an apparatus for controlling the concentration of oxygen and pH of a medium during a bioreaction process in a vessel. The method and apparatus are particularly adapted to a fermentation process. A dissolved oxygen sensor generates a signal corresponding to the pH of the medium and a dissolved oxygen sensor generates a signal corresponding to the dissolved oxygen in the medium. A valve mechanism selectively applies air, $N_2$, $O_2$ and $CO_2$ to the medium. A controller produces a control signal for controlling the operation of the valve means so that a substantially fixed volume of gas consisting of one or more of air, $CO_2$, $N_2$ and $O_2$ are added to the fermenting medium during a period of time. The controller determines in response to the dissolved oxygen and pH signals, the amount of $CO_2$, $O_2$ and/or $N_2$ required to effect dissolved oxygen and pH correction. The controller further adjusts these determined values to compensate for the displacement of the $CO_2$ added. As a result, the effect of the $CO_2$ correction on the dissolved oxygen is substantially minimized.

20 Claims, 4 Drawing Figures

FERMENTOR CONTROL SYSTEM

BACKGROUND OF THE INVENTION

The invention is generally directed to a control system for a tissue culture reactor and in particular to a control system for a tissue culture fermentor which exercises concurrent control of dissolved oxygen content (DO) and pH of a medium in a fermenting vessel containing a tissue culture fermentation. Tissue culture fermenting vessels are used to grow cells attached to microcarriers or free suspension cell cultures in a liquid medium containing the various components needed for cell growth. To create the proper environment for the tissue culture cells to grow rapidly and efficiently, relatively narrow ranges of values for concentrations for certain materials are required. These variables include the acidity of the surrounding medium (pH), amount of dissolved oxygen (DO), as well as the concentration of other materials.

These variables include the acidity of the surrounding medium (pH), amount of dissolved oxygen (DO), as well as the concentration of other materials.

The liquid medium for culture growth is agitated by a stirrer, such as a magnetic stirrer, to maintain an even distribution of materials in the surrounding liquid and to attempt to prevent local accumulations of cells and the presence of concentration gradients which can produce undesirable effects upon the tissue culture cells. Cells from higher organisms growing in microcarrier cultures and free suspension cultures are relatively physically fragile and thus only low speed stirring is possible. As a result, a significant potential of harmful concentration gradients is possible where liquid acids or bases are introduced to the fermenting vessel. This makes control of pH by other than addition of liquids extremely desirable, where possible.

Generally, as a tissue culture fermenting process operates, the oxygen and pH needs of the tissue culture change. As a result, there is a need to adjust the flow of materials into the fermenting vessel at various stages of the fermenting process to maintain the tissue culture cells in an optimal growth environment. In addition to maintaining the environmental conditions within ranges of acceptable values, a consistency of values is desired.

It has been determined that the tissue culture cells are responsive not only to the environmental conditions present in the surrounding liquid, but to changes in the environmental conditions of the liquid medium. Therefore, the tissue culture cells often grow more efficiently in a less stressful environment where rapid changes in the surrounding environment are avoided. Therefore, rapid and repeated changes in the surrounding environment are to be avoided.

Two important environmental conditions in a tissue culture fermentor are the amount of dissolved oxygen present in the liquid medium and the pH in the liquid medium. Traditionally, tissue culture fermentor control systems have independently monitored and controlled the level of dissolved oxygen (DO) and pH in the fermenting vessel. However, the independent control of these variables tends to provide for erratic and stressful changes in the environment surrounding the tissue culture.

In particular, when there is an insufficient amount of dissolved oxygen present in the liquid medium, additional oxygen is added to the medium. This has the effect of stripping $CO_2$ from the medium which raises the pH of the medium (the liquid medium becomes more basic). As a result, the pH level has now shifted away from the desired value and additional $CO_2$ is added to lower the pH (increase the acidity). However, when $CO_2$ is added to the liquid medium, it has the effect of stripping dissolved oxygen out of the medium which again serves to require the addition of oxygen to the liquid medium. This cycle operates out of control and the amount of dissolved oxygen in the liquid and the pH of the liquid tend to follow each other causing a stressful environment for the tissue culture.

Accordingly, there is a need for a control system to provide simultaneous regulation of the amount of dissolved oxygen and the pH of the liquid surrounding the tissue culture in a manner which prevents fluctuations in the concentrations of the dissolved oxygen and the pH which provide a stressful environment for the tissue culture.

SUMMARY OF THE INVENTION

The present invention is generally directed to an apparatus for controlling the dissolved oxygen and pH of a culture medium during a bioreaction process such as fermentation, in a vessel. A dissolved oxygen sensor generates a signal corresponding to the dissolved oxygen in the medium. A pH sensor generates a signal corresponding the pH of the medium. A valve member selectively applies air, $N_2$, $O_2$ and $CO_2$ to the fermenting medium. A controller produces a control signal for controlling the operation of the valve mechanism so that a substantially fixed volume of gas consisting of one or more of air, $CO_2$, $N_2$ and $O_2$ is added to the medium during a period of time. The controller determines in response to the dissolved oxygen and pH signal the amount of $CO_2$, $O_2$ and/or $N_2$ required to effect the dissolved oxygen and pH correction. The controller adjusts these determined values to compensate for the displacement of air as a result of $CO_2$ added so that the effect of the $CO_2$ correction on the dissolved oxygen is substantially minimized.

Accordingly, it is an object of the instant invention to provide an improved tissue culture fermentor controller.

Another object of the invention is to provide an improved tissue culture fermentor conftrol system which reduces the need for constant and radical infusions of dissolved oxygen and carbon dioxide to maintain the environment within prescribed boundaries.

A further object of the invention is to provide a control system which simultaneously controls the amount of dissolved oxygen and the pH in a bioreactor.

Still another object of the invention is to provide a pH-dissolved oxygen control system for a tissue culture fermentor which uses time proportioned control of the flow of air, $N_2$, $O_2$, and $CO_2$ to maintain the pH and amount of dissolved oxygen within narrow ranges of values.

Another object of the invention is to provide a tissue culture fermentor control system which reduces the interaction of the independent outputs of the dissolved oxygen and pH controllers to minimize stressful changes to the medium.

Still other objects and advantages of the invention will in part be obvious and will in part be apparent from the specification.

The invention accordingly comprises the several steps and the relation of one or more such steps with respect to each of the others, and the apparatus embodying features of construction, combinations of elements, and arrangements of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

Figure 1:
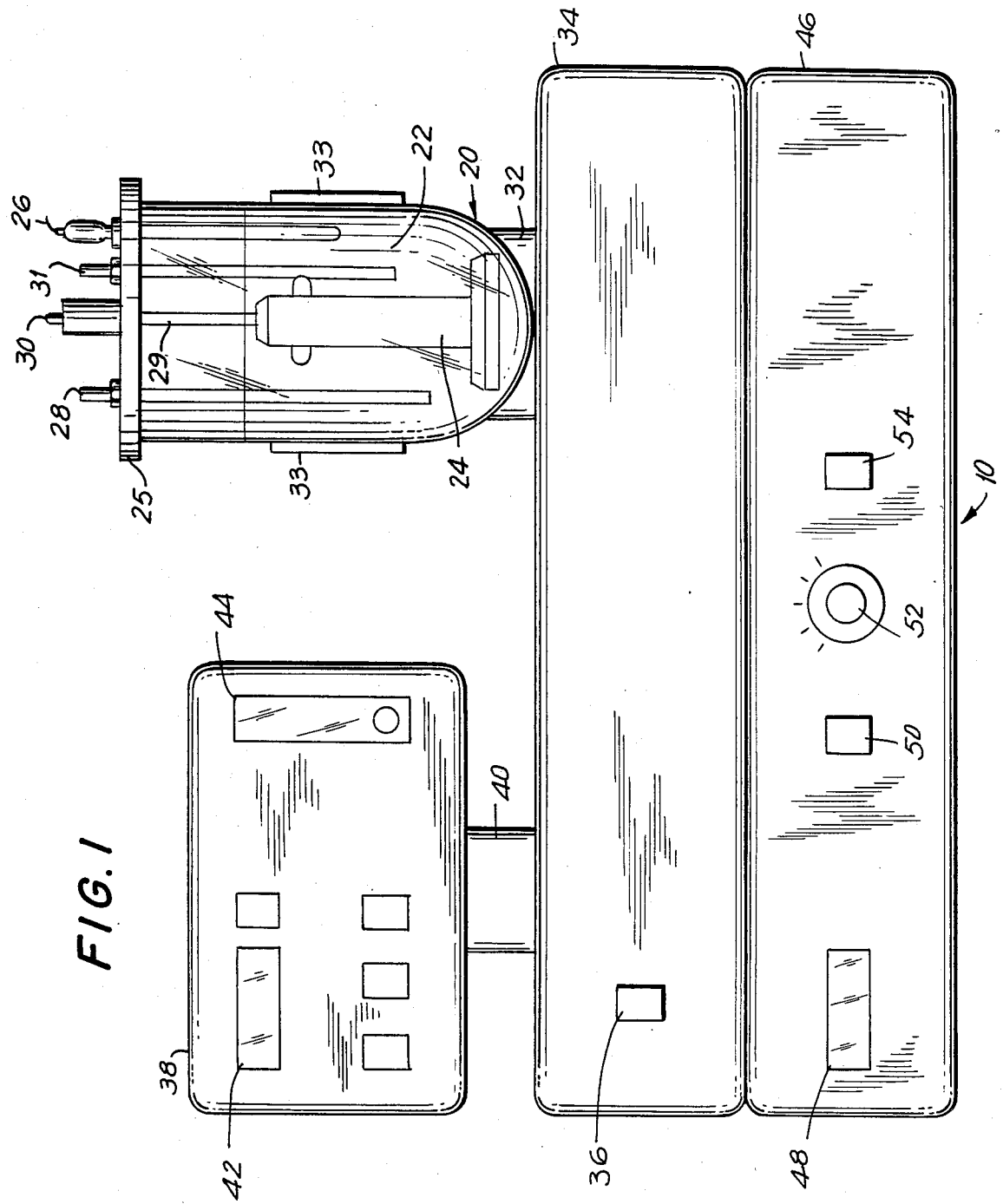
FIG. 1 is a front elevational view of a tissue culture fermenting system, including a control system constructed in accordance with a preferred embodiment of the invention.

Reference is made to FIG. 1 wherein a tissue culture cell fermentation system 10 including a control system constructed in accordance with the invention is depicted. Fermentation system 10 includes a fermentation vessel 20 having a tissue culture and liquid medium 22 contained therein. Vessel 20 contains a magnetically driven agitation system 24 rotatably supported on cover 25 for agitating medium and cell culture 22 in vessel 20. A pH probe 26 extends into vessel 20 through cover 25 and is supported thereby. In a preferred embodiment, pH probe 26 is implemented using glass electrode technology. However, pH probe 26 can be of any type as long as it does not react with the medium or cell culture within fermentation vessel 20. A dissolved oxygen (DO) probe 28 also projects into fermenting vessel 20 through cover 25 and is supported thereby. DO sensor 28 may be a galvanic or polarographic type DO sensor. In a preferred embodiment, DO probe 28 is a galvanic type probe which produces a millivolt signal directly proportional to the rate of oxygen diffusion through its membrane. A gas inlet 30 is provided for fermentation vessel 20 through the drive shaft 29 of agitation system 24, which is adapted to feed the added gases to the medium from near the bottom of the agitation system in a manner which produces substantial dissolving of the gases in the fluid without undue foaming. However, any desired sparging system may be used. An alkaline entry tube 31 also penetrates through cover 25 into vessel 20 to deliver a basic solution or other liquid into medium 22 when required.

Fermenting vessel 20 rests on a base 32 which rests on a main console 34. The vessel is supported by a heater/support member 33. Main console 34 includes a power switch 36 and houses a microprocessor 60 (FIG. 2).

A display console 38 sits on a stand 40 on top of main console 34. Display console 38 includes a digital display 42 for depicting temperature and agitation values. In addition to several other displays, a flow meter 44 is present on the front of display console 38. Main console 34 rests on top of an instrument console 46 which contains a digital display 48 for displaying the amount of dissolved oxygen and the pH of medium 22. Instrument console 46 also has a series of switches 50, 52 and 54 for manually adjusting the set points of the controlled variables. Electrical connection between the sensors, such as pH probe 26 and DO probe 28, and the main console is provided (not shown).

Figure 2:
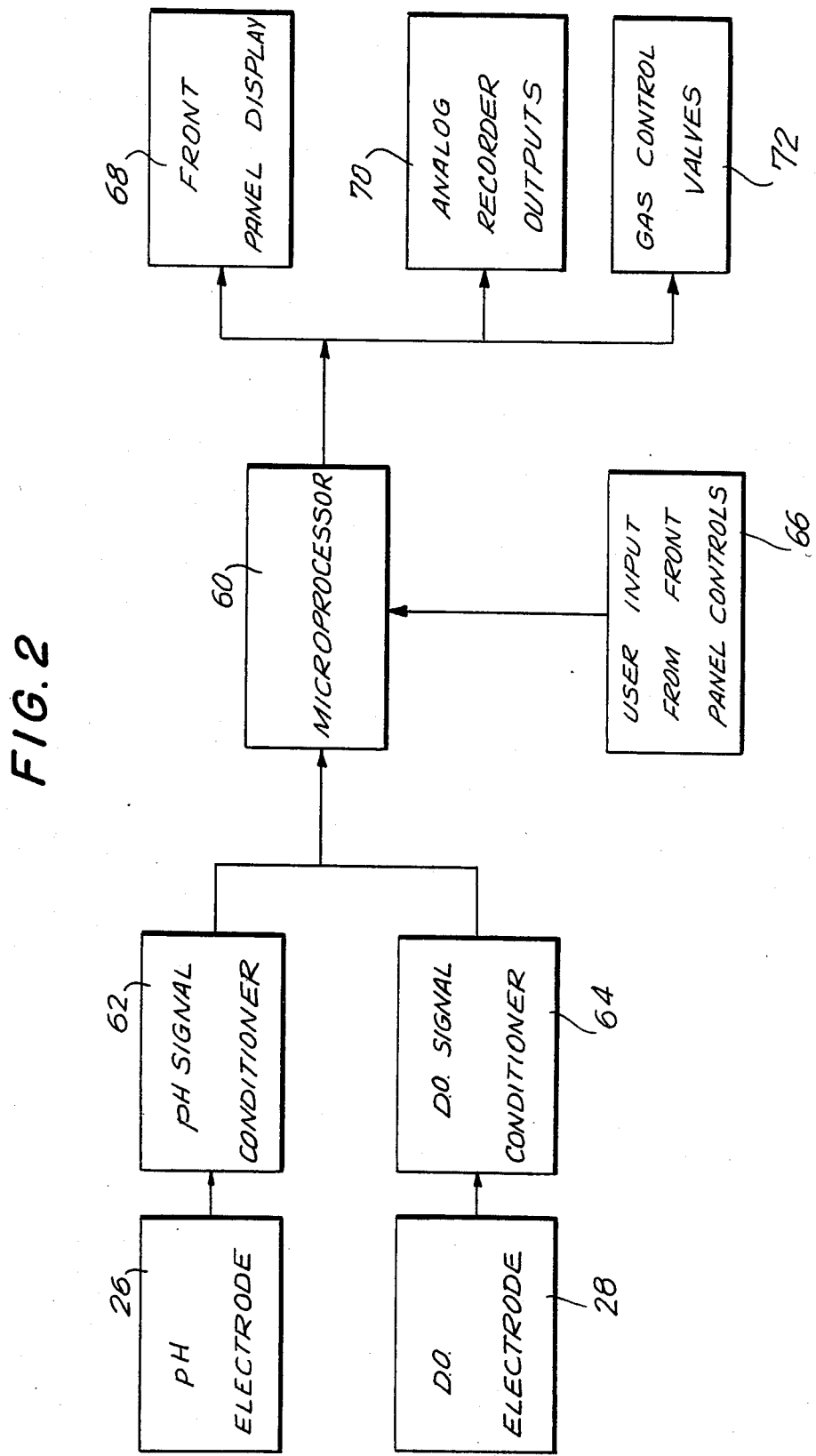
FIG. 2 is a block diagram of the functional elements in a tissue culture fermentor system constructed in accordance with the invention.

Reference is made to FIG. 2 wherein the elements of the control system are depicted. The control system includes a microprocessor 60 which has a central processer unit as well as memory components including a RAM and a ROM (or an EPROM or EEPROM), to store set points, calibration information, programs, data and calculation results. Microprocessor 60 receives inputs from pH probe 26 through a pH signal conditioner 62 and from DO probe 28 through a DO signal conditioner 64.

In a preferred embodiment of the invention, pH signal conditioner 62 and DO signal conditioner 64 convert the analog electrical signal received from probe 26 and DO probe 28, respectively, into a frequency signal through the use of an optical coupler to provide electrical isolation of the pH and DO signals from each other and from the microprocessor. Thereafter, the frequency signals indicative of the pH of the medium and of the DO are input into microprocessor 60. In the preferred embodiment of the invention, the frequency inputs are multiplexed so as to enter microprocessor 60 in a single port. However, separate input ports may also be used.

Microprocessor 60 also receives user inputs from front panel controls 66 which include switches 50, 52 and 54 for adjusting the set points of the pH and DO levels.

Microprocessor 60 outputs signals to front panel display 68 which includes, among other front panel displays flow meter 44 and digital DO and pH display 48. Microprocessor 60 outputs data recorded on microprocessor 60 which is indicative of the environmental state of the medium and cell cultures in fermentation vessel 20 during the period in which the fermentation process is going on to analog recorder outputs 70. Analog recorder outputs 70 allow for a user of the fermenting system to analyze the environmental conditions of the fermentation process or other bioreaction over the life of the process, which can often extend to a period of days or several weeks. In this way, repeatability of a desired reaction can be achieved through emulation of the environmental guideposts of a successful process.

In addition, microprocessor 60 controls the operation of gas control valves 72. Gas control valves 72 are coupled to sources of air, gaseous nitrogen ($N_2$), gaseous oxygen ($O_2$) and gaseous carbon dioxide ($CO_2$). The output of gas control valves 72 are coupled to gas inlet 30 for introduction of the gases into fermentation vessel 20.

Figure 3:
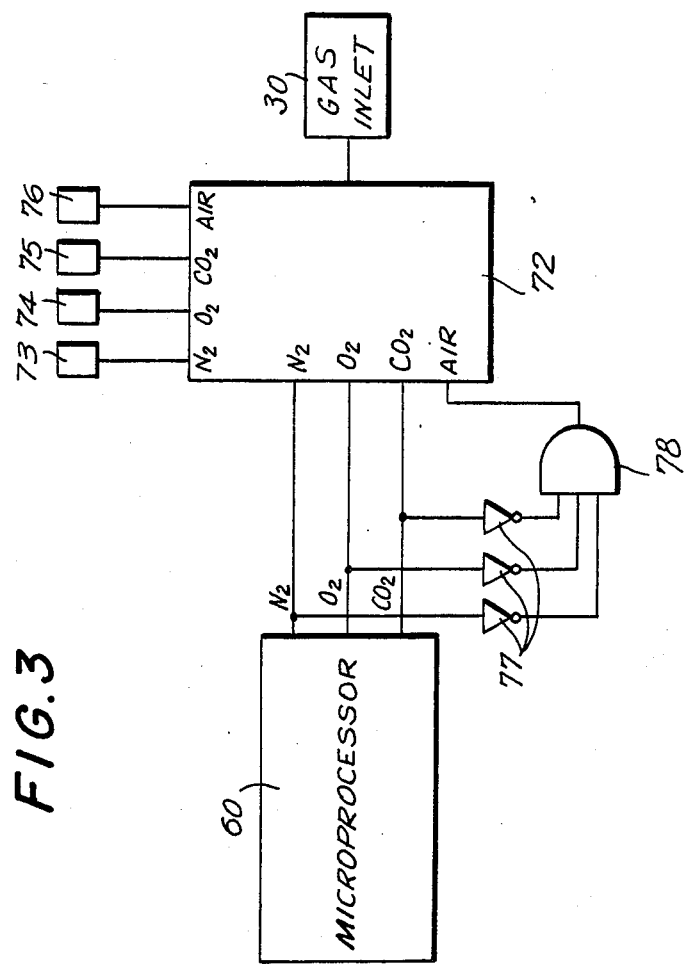
FIG. 3 is a block diagram of a gas control system used in a preferred embodiment of the invention.

Reference is made to FIG. 3 wherein the manner in which gas control valves 72 control the flow of gasses into fermentation vessel 20 is depicted. Microprocessor 60 outputs time variable signals indicative of time periods during which the flow of selected gases are to occur. However, in a preferred embodiment, microprocessor 60 does not output an air signal directly. Rafther, if microprocessor 60 indicates that no $N_2$, $O_2$ or $CO_2$ is to flow into gas inlet 30, air is selected. This can be implemented with a series of inverters 77 and an AND gate 78. Gases are supplied from a source of $N_2$ 73, source of $O_2$ 74, source of $CO_2$ 75 and source of air 76. The gas exiting valves 72 are connected to gas inlet 30 and introduced into fermentation vessel 20.

Figure 4:
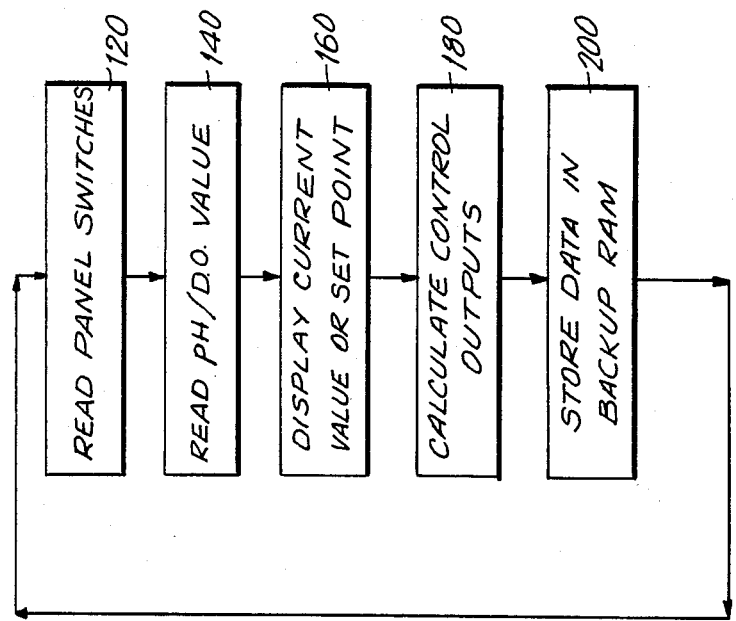
FIG. 4 is a flow diagram of the operation of a tissue culture fermentor control system constructed in accordance with the invention.

Reference is next made to FIG. 4 wherein the cycle followed by microprocessor 60 in implementing the control over the fermentattion system is depicted. Microprocessor 60 reads the front panel switches in block 120 and then reads the pH and DO values in block 140. Next, in block 160 the current value and/or set point of the various variables are displayed on one of the displays on the front panel and output to analog recorder output 70. Next, the control outputs are calculated in block 180 which causes the appropriate flow of gases into fermenting vessel 20. Finally, the data received is stored in a back-up memory unit in step 200 and the cycle repeats itself again beginning at block 120.

The present invention is directed to minimizing the interaction of the independent outputs of the DO and pH controllers which tend to counteract each other and results in relatively large variations in the state of the cell culture process, to the detriment of the process. The interaction is minimized by using the outputs of DO and pH controllers as inputs to a gas flow controller. pH probe 6 in association with pH signal conditioner 62 and DO probe 26 in association with DO signal conditioner 64 act as the DO and pH controllers respectively. Microprocessor 60 in this embodiment acts as the gas flow controller which implements its gas flow decisions by sending signals to gas control valve 72.

Microprocessor 60 performs several functions to act as a gas flow controller. First, it generates positive outputs $\phi_{N_2}$ and $\phi_{O_2}$ which are functions of the current error and all previous errors in DO (except in certain cases described below). In addition, microprocessor 60 generates continuous positive outputs $\phi_{CO_2}$ and $\phi_{ALK}$ which are functions of the current error and all previous errors in pH.

The various "$\phi$" functions are calculated (calculated as described below) from two terms: one term being a term proportional to the present error and the other term being related to an integration of the errors present in the process from its beginning until the present. The error is defined as the difference between the current value of a variable and its set point. The set point is set by an operator by use of front panel controls 66. The set point may be adjusted during the course of the fermentation process by the user. However, it remains the same unless so changed. The "$\phi$" variable is calculated as follows:

$$\phi = K_c \epsilon + K_c (t_m/\tau) \Sigma \epsilon$$

"$K_c$" is a scaling constant used to adjust the value of "$\phi$" based on the capacity of the medium and the length of the gas cycle. "$\epsilon$" represents the error, which is equal to the difference between the current value and the set point. "$t_m$" is a system constant which is representative of the time between measurements of the error.

In a preferred embodiment of the invention, wherein the cycle time is two seconds, $t_m$ is equal to one second. This results in the conversions being asynchronous to the process, thereby reducing the delay between the measurement and the corrective action to about one second. "$\tau$" is the time constant for the integrated term. In a preferred embodiment of the invention $K_c$, $t_m$ and $\tau$ are preset and are not user accessible. However, in another embodiment they may be altered by the user. "$\Sigma \epsilon$" is the sum of the errors measured over the period that the process has been operating.

As a result, the "$\phi$" functions have both a proportional term and an integrated term which attempt to approximate the current demand of the system for the particular variable input. There are, however, certain constraints on the calculation of $\phi$ as defined by the above equation. If the sum of the proportional and integration term is too large, representative of the process starting far from the set point, preset limits are imposed on $\phi$ and the integration is stopped to prevent the carrying through of large corrections where it may provide a destabilizing impact on the process. In addition, the proportional term has a maximum value for each variable and if the proportional term exceeds this value, $\phi$ is limited to this upper value and the integration term is reset to zero. The purpose of the upper value of the proportional term is to prevent over-compensation and dangerously high gradients of input which are particularly stressful to the tissue culture cells. Under such circumstances, the control scheme waits until the tissue culture process is closer to the set point and then starts the above-described control system as if the process was just starting.

In addition, microprocessor 60 generates time proportional outputs $t_{air}$, $t_{N_2}$, $t_{O_2}$ and $t_{CO_2}$ which control the gas flow into the reactor. The gas flow controller operates on the basis of a cycle during which there are two phases. During one phase air is input into fermenting vessel 20 and during the other phase of the cycle one or more of $N_2$, $CO_2$ and $O_2$ in specified volumes are added to fermentation vessel 20. In a preferred embodiment $t_{cycle}$ is equal to two seconds. The cycle time can be varied depending upon the speed at which the fermentation process or other bioreaction proceeds the computing power and memory available and the degree of control desired.

As noted above, $\phi_{N_2}$, $\phi_{O_2}$, $\phi_{CO_2}$ and $\phi_{ALK}$ are positive continuous outputs which are functions of the current error and an estimate of the demand for that variable based on the history of the variable. Only one of $\phi_{N_2}$ and $\phi_{O_2}$ will be positive and only one of $\phi_{CO_2}$ and $\phi_{ALK}$ will be positive. These positive outputs are utilized to control the relative quantity of each of the gasses during each cycle. The volume of gas introduced into fermentation vessel 20 during a cycle 20 is substantially constant within the physical limitations of gas valves 72. As a result, the following equation is used to represent the amount of each of the gasses input into the fermenting vessel during a cycle.

$$t_{cycle} = t_{air} + t_{N_2} + t_{O_2} + t_{CO_2}$$

$t_{air}$ represents the time during the cycle when air is input into the fermentation vessels. The relative values of $t_{air}$, $t_{O_2}$, $t_{CO_2}$ and $t_{N_2}$ are determined as follows. If $\phi_{O_2}$ is greater than zero, then:

$$t_{O_2} = \phi_{O_2} + 0.25 \phi_{CO_2};$$

$$t_{CO_2} = \phi_{CO_2}; \text{ and}$$

$$t_{N_2} = 0.$$

As a result, in this case $t_{cycle} = t_{air} + t_{O_2} + t_{CO_2}$. In this case, however, if $\phi_{CO_2}$ is equal to zero, then:

$$t_{CO_2} = 0; \text{ and}$$

$$t_{cycle} = t_{air} + t_{O_2}.$$

If $\phi_{N2}$ is greater than zero, calculated variable Z ($Z = \phi_{N2} - \phi_{CO2}$) is used. In the situation where $\phi_{N2}$ is greater than and Z is greater than or equal to zero, then:

$$t_{O2} = 0;$$

$$t_{CO2} = \phi_{CO2}; \text{ and}$$

$$t_{N2} = Z.$$

As a result, in this case $t_{cycle} = t_{air} + t_{N2} + t_{CO2}$.

In the situation where $\phi_{N2}$ is greater than zero, and Z is less than zero, then:

$$t_{O2} = -0.25Z;$$

$$t_{CO2}\phi_{CO2}; \text{ and}$$

$$t_{N2} = 0.$$

As a result, in this situation $t_{cycle} = t_{air} t_{O2} + t_{CO2}$.

In the foregoing cases the effect of the added $CO_2$ required for pH correction on the D0 correction, the change in amount of $O_2$ delivered to the system in the air or otherwise by reason of the addition of $CO_2$, is compensated for. In effect, the system compensates for the amount of air displaced by the $CO_2$. In effect, the system compensates for the amount of air displaced by the $CO_2$ by adding air (reduces $N_2$) or adding oxygen, the $N_2$ and $C0_2$ being considered equal inert gases for this purpose.

The final situation, is one in which, where $\phi_{N2}$ and $\phi_{O2}$ are equal to zero and, then;

$$t_{O2} = t_{N2} = 0; \text{ and}$$

$$t_{CO2} = \phi_{CO2}.$$

Therefore, in this case $t_{cycle} = t_{air} + t_{CO2}$.

In this case no compensation for the addition of $CO_2$ is required because DO is at the set point.

Several examples are now described to illustrate the above examples. Where the amount of $CO_2$ required as a result of the pH level is 200 ms. ($\phi_{CO2}$), and the amount of oxygen required as a result of the DO level is 100 ms. ($\phi_{O2}$). The controller calculates the "t" variables as follows:

$$t_{CO2} = 200 \text{ ms.; and}$$

$$t_{O2} = 150 \text{ ms.;}$$

Whereby the air displaced by the $CO_2$ (200 ms.) is compensated for by the addition of an additional 50 ms. of $O_2$. It should be recognized that air essentially consists of 80% $N_2$ and 20% $O_2$ and that for the purpose of DO correction, $CO_2$ can be deemed an inert gas.

A second example is where the pH controller requires 100 ms. of $CO_2$ and the DO controller requires 250 ms. of $N_2$. In this case, $t_{CO2} = 100$ ms. and $t_{N2} = 150$ ms. ($\phi_{N2} - \phi_{CO2}$). The $N_2$ is added by the DO controller to increase the amount of inert gas added instead of oxygen and for the purposes of the DO controller it is not important whether the 250 ms. of inert is all $N_2$ or a combination of $N_2$ or $CO_2$ by adjusting the proportion of inert between $N_2$ and $CO_2$ in this case, both the DO and pH control requirements can be met.

The third example is where the pH controller requires 100 ms. of $CO_2$ and the DO controller requires 50 ms. of $N_2$. In this case $t_{CO2} = 100$, $t_{N2} = 0$ and $t_{O2} = \phi_{O2} + 0.25 (\phi_{CO2} - \phi_{N2})$. In this case, the DO controller only requires 50 ms. of inert gas but the pH controller requires 100 ms. of $CO_2$ (and inert gas with reference to the DO controller). Therefore, an additional 50 ms. of inert $CO_2$ is added which displaces the oxygen which would have been added to the 50 ms. of air displaced.

Therefore, an additional 12.5 ms. of $O_2$ is added to replace the oxygen in the air which will be prevented it by the $CO_2$.

As a result of these calculations the relative periods of time during which the various gases are input into the fermentation vessel is controlled.

When the cells are growing and eating $O_2$, producing acid at a rate equal to the rate at which the gas flow is stripping $CO_2$ from the medium but the cells require more oxygen, the case in which only air and oxygen are added during $t_{cycle}$ is selected. This is not a stable state and occurs only by chance if at all during the fermentation process. On the other hand, early in the cell growth when the air exactly meets the oxygen demand but the cells are not yet producing enough acid, and the carbon dioxide is being depleted too quickly, $t_{cycle}$ is composed of only the addition of air and carbon dioxide.

These two conditions can also be handled by a gas flow controller which independently controls the flow of gases into the fermentation vessel to control pH and DO. However, these situations occur for only a limited portion of the reaction time and during the significant portion of the reaction, when these conditions are not met, a gas flow controller which independently controls the pH and DO would cause the constant fluctuation of environmental conditions resulting from the interaction caused by the addition of $O_2$ or $CO_2$.

Microprocessor 60, may, after determining the values of $t_{O2}$, $t_{CO2}$ and $t_{N2}$ calculates the value $t_{air}$ based on the known constant value of $t_{cycle}$ for any predetermined cycle time. With all four gas times now calculated, the appropriate signals can be sent to gas control valve 72 to send an appropriate amount of the various gases into fermenting vessel 20. However, in the embodiment of FIG. 3, this air calculation is unnecessary as the system defaults air in the absence of an instrument to feed $O_2$, $N_2$ or $CO_2$.

The gas flow controller is implemented in a preferred embodiment as software associated with microprocessor 60. The software is implemented in a read only memory (ROM, PROM, EPROM, or EEPROM) chip. However, the software may be implemented utilizing bubble memory or some other type of non-volatile storage medium.

Gas control valves 72, in a preferred embodiment, are implemented as four solonoid valves. One of the solenoid valves is a three way valve which switches a single outlet between an "air" or a "mixture" flow. The other three valves control the $N_2$, $O_2$ and $CO_2$ sources into the mixture input of the three-way valve.

The user may also elect to remove the fermentation system from the control mode in which the gas flows are controlled and convert the fermentation system to a second mode where only air is inputted into the fermentation vessel.

The present invention has been described with respect to a fermentation process for a tissue culture medium. However, the controller is equally applicable to a hollow fiber process and a glass bead packed column process. All of these processes can be considered bioreactions.

Accordingly, a pH-DO control system particularly adapted for a tissue culture fermentation process is provided which serves to prevent unstable variations in pH and DO during a fermentation reaction by coupling the control of these two variables.

It will thus be seen that the objects set forth above, among those made apparent from the preceding description, are efficiently attained and, since certain changes may be made in carrying out the above process and the constructions set forth, without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as matter of language, might be said to fall therebetween.

What is claimed is:

1. An apparatus for controlling a dissolved oxygen and pH of a medium during a bioreaction process in a vessel, comprising: pH sensing means for generating a signal related to the pH of the medium; dissolved oxygen sensing means for generating a signal related to the dissolved oxygen in the medium; valve means for selectively applying quantities of air, $N_2$, $O_2$ and $CO_2$ to the medium; and control means for producing a control signal for controlling the operation of the valve means so that a substantially fixed volume of gas consisting of one or more of air, $CO_2$, $N_2$ and $O_2$ is added to the medium, said control means determining in response to the dissolved oxygen and pH signals the amount of $CO_2$, $O_2$ and/or $N_2$ required to effect dissolved oxygen and pH correction and calculating from the required amounts the quantities of air, $N_2$, $O_2$ and/or $CO_2$ to compensate for the displacement of air as a result of the $CO_2$ added by adding $N_2$ when the $N_2$ required is greater than the $CO_2$ required, and adding $O_2$ when the amount of $N_2$ required is less than the amount of $CO_2$ required; whereby the effect of the $CO_2$ correction on the dissolved oxygen is substantially minimized.

2. The apparatus of claim 1, wherein the process is a fermentation process and the medium is a fermentation medium.

3. The apparatus of claim 1, wherein the control means compensates for the displacement of air as a result of the $CO_2$ added by adding an amount of $N_2$ substantially equal to the amount of $N_2$ required minus the amount of $CO_2$ required, and adding $O_2$ when the amount of $N_2$ required is less than the amount of $CO_2$ required, in an amount equal to one-quarter of the difference between the required $N_2$ and $CO_2$.

4. The apparatus of claim 1, wherein the period of time is divided into a first section and a second section, such that during the first section air is added to the medium and during the second section amounts of gases selected from $N_2$, $O_2$ and $CO_2$ are added to the medium.

5. The apparatus of claim 1, wherein air is added to the medium unless there is a need to add one or more of $N_2$, $O_2$ and $CO_2$.

6. The apparatus of claim 1, wherein the control means include error calculating means for generating pH and dissolved oxygen control outputs determined from at least one of present pH error, dissolved oxygen error and historical errors during the process, respectively, the difference between the detected values of dissolved oxygen and pH and set points for dissolved oxygen and pH being the respective errors; and gas flow control means coupled to the error calculating means for calculating needed inputs to the medium to control the pH and dissolved oxygen determined from the pH and dissolved oxygen control outputs.

7. The apparatus of claim 6, wherein the error calculating means generates the pH and dissolved oxygen control outputs by summing a term proportional to the current error and a term determined from at least one of the present error and the sum of at least a portion of the errors occurring earlier in the process.

8. The apparatus of claim 6, wherein the pH and dissolved oxygen control outputs have respective cutoff points which they are restrained from exceeding.

9. The apparatus of claim 8, wherein the term determined from the sum of the errors occurring earlier in the fermentation process ceases to include the current error when the sum of the two terms exceeds the cutoff value.

10. The apparatus of claim 8, wherein the term related to the sum of the errors occurring earlier in the process is set to zero when the term proportional to the current error exceeds the cutoff point.

11. The apparatus of claim 9, whrein the term determined from the sum of the errors during the process is set to zero when the term proportional to the current error exceeds the cutoff point.

12. The apparatus of claim 2, wherein the medium is a tissue culture medium.

13. The apparatus of claim 1, wherein the pH sensing means is a glass electrode pH probe.

14. The apparatus of claim 1, wherein the dissolved oxygen sensing means is a galvanic type dissolved oxygen sensor.

15. The apparatus of claim 1, wherein the control means in implemented as a microprocessor with firmware.

16. The apparatus of claim 1 further comprising front panel display means for displaying dissolved oxygen and pH values.

17. The apparatus of claim 1 further comprising analog recording means for recording the state of the bioreaction process, the state of the process including the values of the dissolved oxygen, pH, their respective setpoints and a breakdown of the substantially fixed volume of gas delivered to the medium in the period of time.

18. The apparatus of claim 1, wherein the valve means include valves for selecting from among air, $O_2$, $CO_2$ and $N_2$.

19. The apparatus of claim 6 further comprising user input means for adjusting the set points.

20. A method for controlling the dissolved oxygen and pH of the medium during a bioreaction process in a vessel comprising: detecting the pH of the medium; detecting the dissolved oxygen in the medium; selecting a mixture of air, $N_2$, $O_2$ and $CO_2$ to be introduced to the medium in a period of time by determining the amounts of $CO_2$, $O_2$ and/or $N_2$ required to effect dissolved oxygen and pH correction determined from the dissolved oxygen and pH in the medium detected and calculating the mixture of air, $N_2$, $O_2$ and $CO_2$ to compensate for the displacement of air as a result of the $CO_2$ added by adding $N_2$ when the $N_2$ required is greater than the $CO_2$ required, and adding $O_2$ when the amount of $N_2$ required is less than the amount of $CO_2$ required; whereby the effect of the $CO_2$ correction on the dissolved oxygen is substantially minimized.

* * * * *